(12) United States Patent
Bestetti et al.

(10) Patent No.: US 6,413,244 B1
(45) Date of Patent: *Jul. 2, 2002

(54) CATHETER SYSTEM FOR SKIN PASSAGE UNITS

(75) Inventors: Gilberto E. Bestetti, Schliern bei Köniz; Thomas Frei, Lützelflüh; Andreas Reinmann, Bern, all of (CH)

(73) Assignee: Disetronic Licensing AG, Burgdorf (CH)

(*) Notice: Subject to any disclaimer, the term of this patent is extended or adjusted under 35 U.S.C. 154(b) by 0 days.

This patent is subject to a terminal disclaimer.

(21) Appl. No.: 09/460,144

(22) Filed: Dec. 13, 1999

Related U.S. Application Data

(63) Continuation of application No. 09/048,756, filed on Mar. 26, 1998, now Pat. No. 6,071,265.

(30) Foreign Application Priority Data

Mar. 26, 1997 (CH) .................................................. 0727/97

(51) Int. Cl.⁷ .................................................. A61M 5/14
(52) U.S. Cl. ........................................ 604/256; 604/175
(58) Field of Search ................................ 604/256, 533, 604/245–246, 523, 905, 174–175, 244, 93.01

(56) References Cited

U.S. PATENT DOCUMENTS

| | | |
|---|---|---|
| 1,899,492 A | 2/1933 | Beebe |
| 3,783,868 A | 1/1974 | Bokros |
| 3,970,089 A | 7/1976 | Saice |
| 4,436,519 A | 3/1984 | O'Neill |
| 4,475,548 A | 10/1984 | Muto ..................... 128/207.14 |
| 4,682,981 A | 7/1987 | Suzuki et al. |
| 4,866,501 A | 9/1989 | Johnston et al. |
| 4,880,412 A | 11/1989 | Weiss .......................... 604/165 |
| 4,966,588 A | 10/1990 | Rayman et al. |
| 5,033,476 A | 7/1991 | Kasai .......................... 128/764 |
| 5,092,849 A | 3/1992 | Sampson |
| 5,098,397 A * | 3/1992 | Svensson et al. ........... 604/174 |
| 5,100,394 A | 3/1992 | Dudar et al. |
| 5,104,389 A | 4/1992 | Deem et al. ................. 604/264 |
| 5,209,739 A | 5/1993 | Talalay ........................ 604/195 |
| 5,281,199 A | 1/1994 | Ensminger et al. ........... 604/93 |
| 5,306,255 A | 4/1994 | Haindl |
| 5,324,270 A | 6/1994 | Kayan et al. ................ 604/167 |
| 5,407,434 A | 4/1995 | Gross |
| 5,429,609 A | 7/1995 | Yoon |
| 5,460,616 A | 10/1995 | Weinstein et al. ........... 604/167 |
| 5,466,230 A | 11/1995 | Davila |
| 5,514,109 A | 5/1996 | Mollenauer et al. |
| 5,522,803 A | 6/1996 | Teissen-Simony .......... 604/177 |
| 5,545,143 A | 8/1996 | Fischell |
| 5,634,911 A | 6/1997 | Hermann et al. |
| 5,634,937 A | 6/1997 | Mollenauer et al. |
| 5,782,817 A | 7/1998 | Franzel et al. ............... 604/256 |
| 5,800,390 A | 9/1998 | Hayakawa et al. |
| 5,814,026 A | 9/1998 | Yoon ........................... 604/280 |
| 6,010,494 A | 1/2000 | Schäfer et al. .............. 604/533 |

FOREIGN PATENT DOCUMENTS

| | | |
|---|---|---|
| EP | B0302076 | 4/1987 |
| EP | B0398950 | 1/1989 |

* cited by examiner

*Primary Examiner*—Brian L. Casler
*Assistant Examiner*—LoAn H. Thanh
(74) *Attorney, Agent, or Firm*—Dorsey & Whitney LLP

(57) ABSTRACT

Catheter system consisting of a sleeve, a catheter and a membrane partially arranged in the sleeve, which can be fixed in a skin passage unit in such a way that the catheter protrudes from the skin passage unit towards the interior of the body, wherein the individual components of the catheter system are inseparably connected to one another.

9 Claims, 2 Drawing Sheets

CATHETER SYSTEM FOR SKIN PASSAGE UNITS

This application is a continuation of U.S. patent application Ser. No. 09/048,756, filed Mar. 26, 1998, now issued as U.S. Pat. No. 6,071,265, issued on Jun. 6, 2000, which is hereby incorporated herein by reference.

PRIORITY CLAIM

This application claims priority of Swiss patent application 1997 0727/97, filed Mar. 26, 1997, which hereby fully is incorporated herein by reference.

BACKGROUND OF THE INVENTION

1. Field of the Invention

The invention refers to a catheter system consisting of a sleeve, a catheter and a membrane partially arranged in the sleeve, which can be fixed in a skin passage unit in such a way that the catheter protrudes from the skin passage unit towards the interior of the body, wherein the individual components of the catheter system are inseparably connected to each other.

2. Description of the Related Art

Single and multi-lumen catheters made from extruded plastic and cut to a standard length are known. The catheter tip, arranged at the release site of the drug in the human or animal body, is rounded to such an extent that, as far as possible, the hazard of damaging the vessels or the intestinal skin in the abdominal cavity is avoided. The catheter is purposely produced by the manufacturer in a size exceeding the required length so that the catheter can be shortened to the required length during an operation by cutting away the superfluous part. The catheter end created by the cutting process is subsequently formed into a funnel shape to allow a couple with an infusion set inside a port chamber.

U.S. Pat. No. 5,306,255 and European patent EP-B-0 302 076 describe subcutaneous and percutaneous port bodies. These port bodies serve to connect an infusion hose situated outside of the human or animal body to a port catheter situated inside the human or animal body. External embodiments of such port bodies are sufficiently described in the aforementioned patent specifications and we therefore refer to these specifications at this point.

European patent EP-B-0 398 950 describes the internal design of a port body, the port chamber. The port chamber consists of a membrane chamber with two opposing apertures, a membrane made from a flexible material and arranged between these two apertures, containing a connecting channel in its center between the two apertures of the chamber. One aperture serves to accommodate an external infusion hose while a post catheter is located at the other aperture.

In the known devices, the port catheter is connected to the port chamber in such a way that after one end of the catheter has been formed into a funnel shape, the rounded end of the port catheter tip is pushed through the port until the funnel-shaped part of the port catheter wedges itself in the respective aperture of the port body.

The disadvantage of the known systems is that for the mechanical finishing of the catheter end, resulting in the said funnel shape, a special device is needed whose operation requires prior training. The device must be available in every hospital, resulting in purchasing, maintenance, cleaning and sterilization costs. The finishing of the catheter end also takes up a certain time during the operation. Furthermore, the functionality after the reshaping of the catheter end can only be checked visually in the operating theater.

After having been prepared as specified above, the catheter end must be pushed through the port body into its end position. This requires asserting some force directly on the previously prepared catheter end. As a result the catheter end may be damaged, soiled or incorrectly assembled, causing the drug channel to be blocked. A further disadvantage is that the functionality can only be checked after its installation.

SUMMARY OF THE INVENTION

The invention aims to remedy these disadvantages. The object of the invention is to provide a catheter system for administering drugs that neither requires nor permits a mechanical finishing of a catheter end by the operator, that is simple and secure to handle and allows a quick implantation. The function of the catheter system must also be tested outside of the port and before its implantation.

The invention solves the set task with a catheter system consisting of a sleeve, a catheter and a membrane partially arranged in the sleeve, which can be fixed in a skin passage unit in such a way that the catheter protrudes from the skin passage unit towards the interior of the body, wherein the individual components of the catheter system are inseparably connected to each other.

The invention offers the principle advantages that a mechanical finishing of the catheter by the operator during the operation is neither required nor possible, and that it allows a simple and rapid handling of the catheter system fixing inside the port body.

BRIEF DESCRIPTION OF THE DRAWINGS

A preferred embodiment of the invention is shown in the figures, in which.

DESCRIPTION OF THE PREFERRED EMBODIMENTS

Hereinafter the term "inside" will mean "within the human or animal body" and "outside" will mean "outside of the human or animal body."

Figure 1:
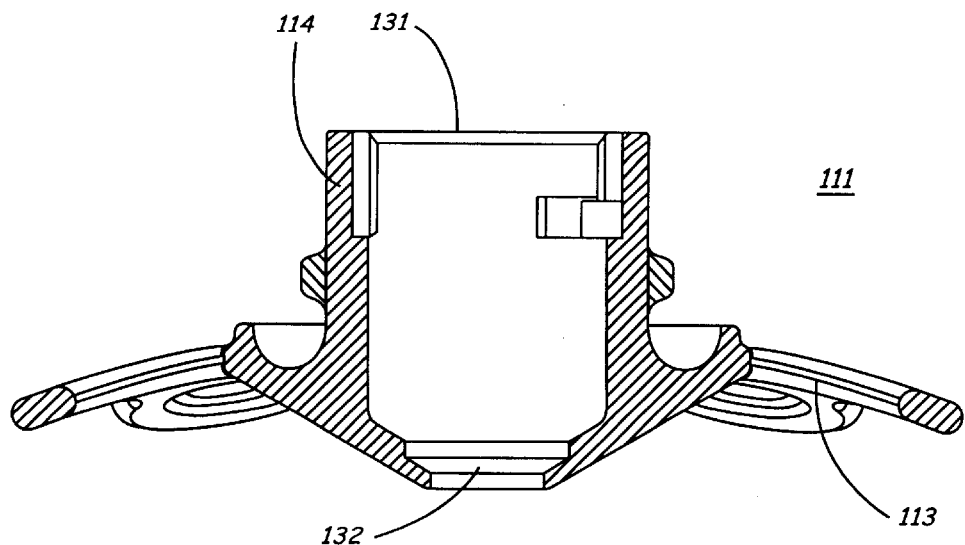
FIG. 1 represents a port body.
Figure 2:
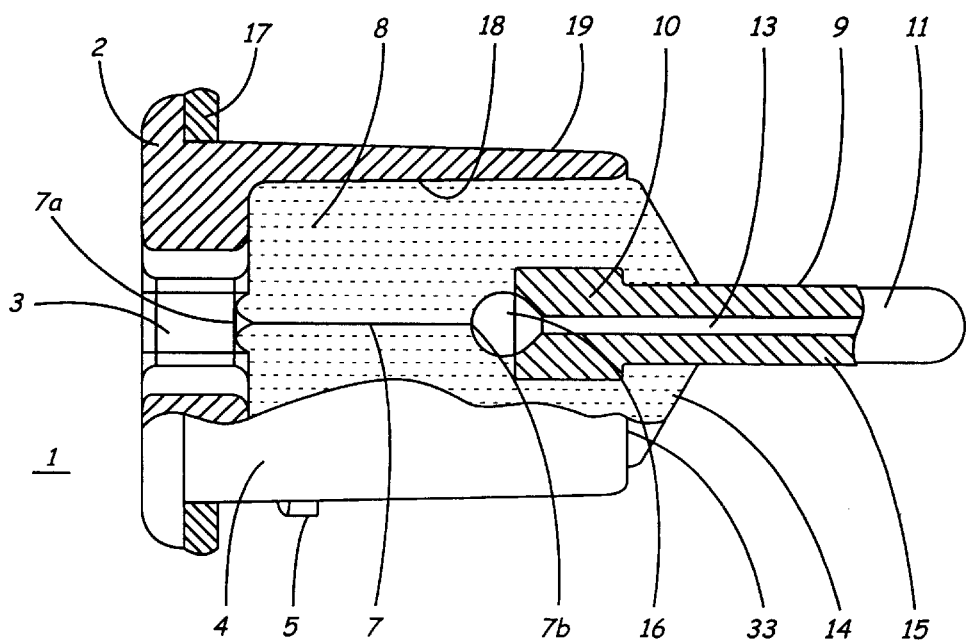
FIG. 2 represents a catheter system according to the invention.
Figure 3:
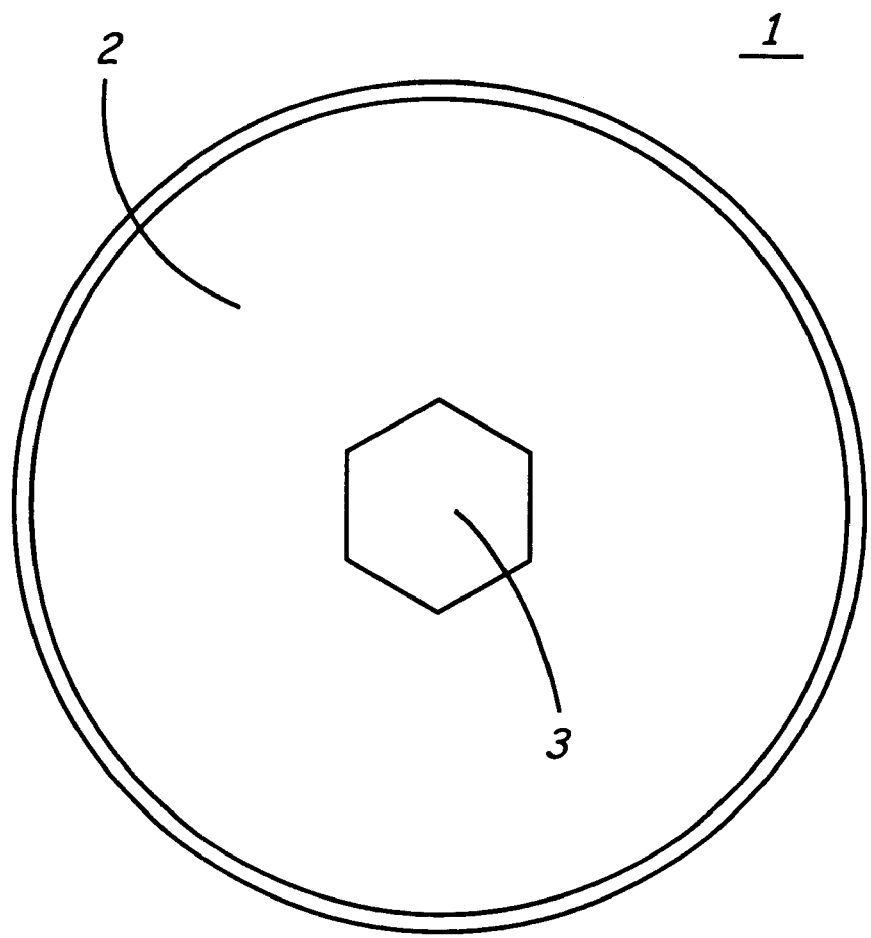

As shown in FIGS. 1 and 2, a closing sleeve 4 of a catheter system 1 is inserted into a port body 111 which alternatively may be called a skin passage unit the port body 111 consists of a hollow cylindrical sleeve portion 114 and a radial anchoring plate 113 arranged on the sleeve. The port body 111 contains two opposing apertures 131, 132. An aperture 131 facing towards the outside corresponds to the internal diameter of the hollow cylindrical sleeve portion 114. The second aperture 132 is located at the end of port body 111 and closes off in a conical shape.

As shown in FIG. 2, the catheter system 1 consists of a hollow cylindrical closing sleeve 4, a cylinder-shaped membrane 8 partially arranged in the closing sleeve 4 and a hose-shaped catheter 9.

The catheter 9 is preferably made from a biocompatible plastic and may be divided into three sections: a catheter head 10, a hose-shaped interim section 15 and a rounded end section 11. A continuous drug channel 13 runs through the inside of the catheter 9.

The outer diameter of the catheter head 10 is larger than that of the hose-shaped interim section 15. The transition between the catheter head 10 and the interim section 15 is preferably designed as steep.

The inner part of the catheter head 10 is funnel-shaped, ending in the drug channel 13.

The closing sleeve 4 has a cylindrical structure and contains two opposing apertures 3, 33. The aperture 3, facing towards the outside, is located in the center of a cover 2, providing the external seal of the closing sleeve 4. The second aperture 33, facing towards the inside, corresponds to the internal diameter of the closing sleeve 4.

The membrane 8 fills the closing sleeve 4 and overlaps the aperture 33 in such a way that it closes off the closing sleeve 4 in a conical shape 14. The membrane is preferably produced from a flexible plastic such as silicone or polyurethane. The center of the membrane contains a self-closing connecting channel 7. An inlet aperture 7a of the connecting channel 7, facing towards the outside, is located at the aperture 3 of the cover 2 while an outlet aperture 7b of the connecting channel 7 is located inside the membrane. The catheter head 10 is arranged at the outlet opening 7b so that the closing sleeve 4, the membrane 8 and the catheter 9 form one integral unit.

The closing sleeve 4 surrounds the membrane 8 containing the catheter head 10 in such a way that the membrane 8 and the catheter head 10 are centrically held together between the cover and the internal wall 18 of the closing sleeve with a defined initial pressure.

The external casing 19 of the closing sleeve 4 contains up to three closing cams of closing elements so that the closing sleeve 4 and thus the entire catheter system 1 can be installed in a respectively designed cylindrical sleeve portion 114 of port body 111. The diameter of the cover 2 of the closing sleeve 4 corresponds to the external diameter of the sleeve portion 114 of port body 111. A closing seal 17 arranged between the cover 2 and the sleeve portion 114 of port body 111 ensures that no dirt or bacteria can enter between the port housing 114 and the closing sleeve 4.

The closing sleeve 4 is preferably produced from injection-molded plastic. This allows a skin-like color to already be applied to the closing sleeve 4 or at least the cover 2 during manufacture, making the externally visible cover 1 less noticeable.

The requirement for a correct catheter length will be met by producing the catheter 9 in various lengths.

The catheter system 2 according to the invention is installed in a port body 111 in such a way that the catheter 9 is first pushed through the respective opening 132 of the port housing 114. As soon as the conically shaped section 14 of the membrane 8 pushes against the internal wall of the port housing 114, the locking cams 5 arranged on the external casing 19 of the closing sleeve 4 are anchored in a respective recess or counter elements of the internal casing of the port sleeve portion 114 of the port body 111 by a slight rotation of the closing sleeve 4. The hexagonal socket shape of the cover aperture 3 allows the slight rotation of the closing sleeve 4. Naturally also other key forms are feasible.

To release drugs from a container into a human or animal body, an infusion hose is pushed from the outside through the opening 3 of the lid 2 and through the connecting channel 7 to the catheter head 10. In order to secure the infusion hose in this connection, the end of the infusion hose can be designed in such a way that it is retained in a respective recess 16 between the membrane 8 and the catheter head 10.

Once the infusion hose is removed, the aperture 3 can be closed with a cover.

We claim:

1. A catheter system for use with a skin passage unit connected to a patient's body, said catheter system comprising:
    a generally cylindrical sleeve having a substantially continuous cylindrical wall, a first end substantially closed by a cover and an open second end generally opposite the first end, said wall and cover substantially defining an interior space;
    a membrane material mounted in and generally filling the interior space, said membrane material having an elongated, generally central, self-closing connection channel extending from the cover to the open end of the sleeve; and
    a catheter having a first end, a second end, a length extending between said ends and a generally central channel, said first end of the catheter mounted in the membrane material, the central channel of the catheter generally aligned with the connection channel of the membrane material, said catheter extending from the sleeve at the open second end, whereby the catheter system can be removably received in the skin passage unit with the catheter protruding from the skin passage unit into the interior of the body.

2. The catheter system according to claim 1, wherein said membrane material is inseparably mounted in the sleeve and the catheter is inseparably mounted in the membrane material.

3. The catheter system according to claim 2, wherein said cover has a generally central aperture, said aperture, connection channel and central channel generally linearly aligned.

4. The catheter system according to claim 1, wherein the skin passage unit comprises a hollow cylindrical sleeve with a first substantially open end and a second end, said hollow cylindrical sleeve having an inside diameter generally corresponding to the outside diameter of the sleeve of the catheter system.

5. The catheter system according to claim 4, wherein a portion of the membrane material extends beyond the catheter system sleeve through the open second end, whereby when said catheter system is installed in the skin passage unit, said portion of the membrane material is adjacent to the second end of the sleeve of the skin passage unit and said cover is adjacent to the first end of the sleeve of the skin passage unit.

6. The catheter system according to claim 1, wherein said membrane material comprises a silicone material, and connects the sleeve and the catheter.

7. A system for administering substances to a body comprising:
    a skin passage unit comprising a port body comprising a hollow cylindrical sleeve portion and an anchoring plate, said anchoring plate connected to and generally radially arranged around said sleeve portion, said sleeve portion formed by a generally cylindrical wall having an inside surface and an outside surface and having a first substantially open end and a second end; and
    a catheter system for being removably received in the skin passage unit, said catheter system comprising:
        a generally cylindrical closing sleeve having a substantially continuous cylindrical wall, a first end substantially closed by a cover portion and an open second end generally opposite the first end, said wall and cover portion substantially defining an interior space;

a membrane mounted in and generally filling the interior space, said membrane having an elongated, generally central, self-closing connection channel extending from the cover portion in the direction of the open end of the closing sleeve, a portion of the membrane extending through the open end of the closing sleeve; and
  a catheter having a first end, a second end, a length extending between said ends and a generally central channel, said first end of the catheter mounted in the membrane, the central channel of the catheter generally aligned with the connection channel of the membrane, said catheter extending from the closing sleeve at the open second end, whereby the catheter system can be removably received in the skin passage unit with the catheter protruding from the skin passage unit into the interior of the body.

8. The system according to claim 7, wherein the membrane material extends from the open second end of the sleeve in a generally conical shape.

9. The system according to claim 8, wherein said conical shape is generally complimentary to the inner end of the skin passage unit, whereby when the catheter system is received in the skin passage unit, the membrane material generally fills and seals the inner end of the skin passage unit.

* * * * *

UNITED STATES PATENT AND TRADEMARK OFFICE
CERTIFICATE OF CORRECTION

PATENT NO.    : 6,413,244 B1
DATED         : July 2, 2002
INVENTOR(S)   : Gilberto E. Bestetti et al.

It is certified that error appears in the above-identified patent and that said Letters Patent is hereby corrected as shown below:

Column 3,
Line 26, please delete "cover" and insert -- cover 2 -- therefor.
Line 30, please delete "of closing elements" and insert -- or closing elements -- therefor.
Line 37, please delete "port housing 114" and insert -- sleeve portion 114 of port body 11 -- therefor.
Line 46, please delete "system 2" and insert -- system 1 -- therefor.
Line 49, please delete "port housing 114" and insert -- port body 111 -- therefor.
Line 51, please delete "port housing 114" and insert -- port body 11 -- therefor.
Line 60, please delete "opening 3" and insert -- aperture 3 -- therefor.
Line 60, please delete "lid 2" and insert -- cover 2 -- therefor.

Signed and Sealed this

Fourth Day of February, 2003

JAMES E. ROGAN
*Director of the United States Patent and Trademark Office*